(12) United States Patent
Park et al.

(10) Patent No.: US 7,767,226 B2
(45) Date of Patent: Aug. 3, 2010

(54) CALCIUM SULFATE BASED NANOPARTICLES

(75) Inventors: YoungBum Park, Amherst, NY (US);
Rosemary Dziak, Amherst, NY (US);
Robert J. Genco, Amherst, NY (US);
Mark Swihart, Williamsville, NY (US);
Hiran Perinpanayagam, London (CA)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 12/011,930

(22) Filed: Jan. 30, 2008

(65) Prior Publication Data
US 2008/0213359 A1    Sep. 4, 2008

Related U.S. Application Data

(60) Provisional application No. 60/887,184, filed on Jan. 30, 2007, provisional application No. 60/887,859, filed on Feb. 2, 2007.

(51) Int. Cl.
*A61K 9/20* (2006.01)
*A61K 9/14* (2006.01)
*A01N 59/06* (2006.01)

(52) U.S. Cl. .......... 424/464; 424/696; 424/489
(58) Field of Classification Search .......... None
See application file for complete search history.

(56) References Cited

U.S. PATENT DOCUMENTS

| | | | | |
|---|---|---|---|---|
| 6,030,636 | A * | 2/2000 | Randolph et al. | 424/426 |
| 2004/0220681 | A1 * | 11/2004 | Cole et al. | 623/23.62 |
| 2005/0251149 | A1 * | 11/2005 | Wenz | 606/94 |
| 2006/0154063 | A1 * | 7/2006 | Fujihara et al. | 428/373 |
| 2006/0233851 | A1 * | 10/2006 | Simon et al. | 424/422 |

FOREIGN PATENT DOCUMENTS

WO    WO 9117722 A1 * 11/1991

\* cited by examiner

*Primary Examiner*—Cherie M Woodward
(74) *Attorney, Agent, or Firm*—Hodgson Russ LLP

(57) ABSTRACT

The present invention provides a method for facilitating repair of an area of bone by providing hemihydrate calcium sulfate particles, mixing the particles with an aqueous solution to obtain a paste, applying the paste to an area of bone in need of repair, and allowing the paste to set.

15 Claims, 9 Drawing Sheets

Mean diameter of crystals in CS and nCS groups

SEM images of nCS-hemi-ß

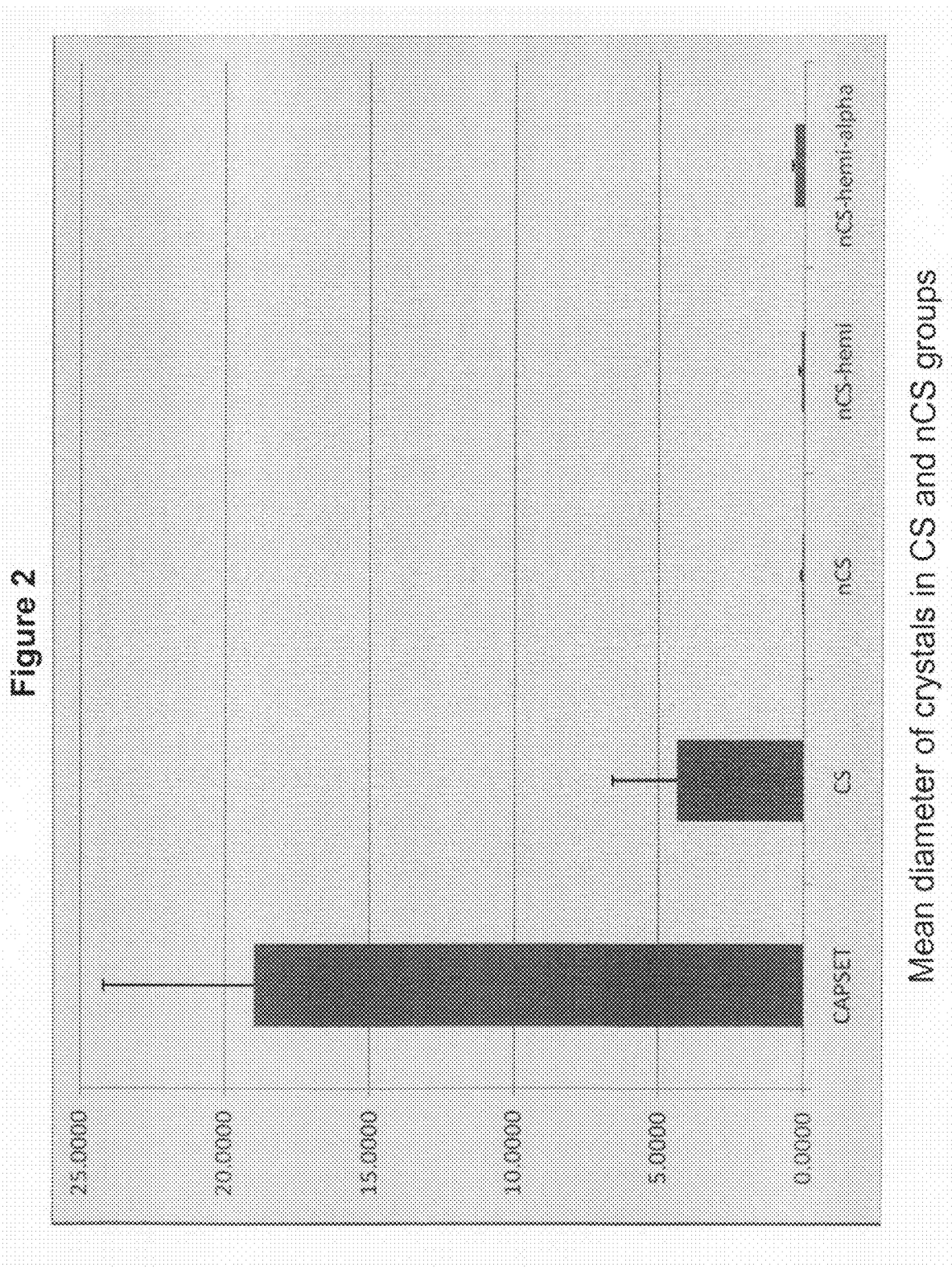

FTIR absorbance shows the difference between dihydrate and hemihydarte form of CS and nCS XRD results of nCS-dihydrate form and nCS-ß hemihydrate form

CALCIUM SULFATE BASED NANOPARTICLES

This application claims priority to U.S. application Ser. No. 60/887,184, filed on Jan. 30, 2007, and to U.S. application Ser. No. 60/887,859, filed on Feb. 2, 2007, the disclosures of each of which are incorporated herein by reference.

FIELD OF THE INVENTION

The present invention relates generally to the field of bone repair and more particularly to a method of repairing bone using improved calcium sulfate preparations.

DISCUSSION OF RELATED ART

Bone regeneration in areas of bone defects occurs very slowly without the aid of osteoconductive or osteoinducing agents that fill in the defect and induce bone tissue growth, which prevents soft tissue growth within the damaged area. Although autogenous bone grafts have the advantage of histocompatibility and are therefore a preferred material for bone regeneration and repair, availability of autogenous material is generally very limited. Allogenic bone is the closest alternative. However allogenic bone has the potential to transmit diseases and trigger immune responses, which are significant disadvantages. Synthetic bone graft materials are alternatives to autogenous and allogenic bone. These include calcium phosphates, calcium sulfate, hydroxyapatite, bioglass, polymers and several combinations of bone derivatives (Griffith, et al. Science, 2002, 295:8, 1009-1014; Orban, et al., Tissue Engineering, 2002, 529-539). Calcium sulfate has been used for more than 100 years in dentistry and medicine. In its hemihydrate form, it has been used as a bone graft material and has been demonstrated in animal and clinical studies to function as an osteoconductive scaffold that can improve bone regeneration (Sidqui, et al. Biomaterials, 1995, 126, 1327; Thomas et al., Calcium Sulfate, 2005, 15(6)599-607). However, there are several drawbacks of conventional synthetic graft materials, including brittle handling properties, variable rates of resorption, which potentially induce adverse effects on bone remodeling due to slow or no resorption of grafted materials, and limited osteoconductive capabilities. Thus, there remains an ongoing need to provide improved methods of treating damaged bone.

SUMMARY OF THE INVENTION

The present invention provides a method for facilitating repair of damaged areas of bone. The method comprises providing a composition comprising hemihydrate calcium sulfate nanoparticles, mixing the composition with an aqueous solution to obtain a paste, applying the paste to an area of damaged bone in need of repair, and allowing the paste to set in the damaged area.

The nanoparticles of hemihydrate calcium sulfate (nCS) used in the present invention are crystalline in nature. Compositions that are used for mixing with an aqueous solution according to the method comprise hemihydrate nCS particles, wherein at least 50% of the hemihydrate nCS particles in the composition have diameters of from approximately 50 nanometers (nm) to 500 nm, inclusive of the recited upper and lower diameter size limits. The compositions may comprise hemihydrate nCS particles in an α isoform (nCS-hemi-α), a β isoform (nCS-hemi-β), or in combinations thereof.

In different embodiments, at least 60%, 70%, 80%, 90% or 95% of the nCS hemihydrate particles in the composition have diameters of from approximately 50 nm to 500 nm.

In one embodiment, at least 50% of the nanoparticles in the composition are β form nanoparticles and have diameters of from 50 nm to 250 nm. In alternative embodiments, at least 60%, 70% or 80% of the particles in the composition have diameters of from approximately 50 nm to 250 nm.

In another embodiment, the composition comprises nCS hemihydrate α isoform nanoparticles, wherein at least 50% of the nanoparticles in the composition have diameters of from 200 nm to 500 nm. In alternative embodiments, at least 50%, 60% or 70% % of the α isoform nCS particles have diameters of from approximately 200 nm to 400 nm.

The composition that is applied to damaged area of bone may comprise additional agents to promote formation of new bone in the damaged area. For example, growth factors may be included in the composition. In one embodiment, the composition comprises platelet-derived growth factor (PDGF).

BRIEF DESCRIPTION OF THE FIGURES

FIG. 2 provides a graphical representation of particle diameter size distributions for calcium sulfate (CAPSET), medical grade calcium sulfate, nCS-dihydrate, nCS-hemi in β form (nCS-hemi-β), and nCS-hemi in α form (nCS-hemi-α).

DETAILED DESCRIPTION OF THE INVENTION

Figure 1A:
FIGS. 1A and 1B provide photographic representations of scanning electron micrograph (SEM) images of nano-particulate calcium sulfate (nCS) as a hemi-hydrate β form (nCS-hemi-β) at 50,000× and 20,000× magnification, respectively.

The present invention provides a method for facilitating repair of a damaged area of bone. The method comprises the steps of providing a composition comprising nanoparticles of hemihydrate calcium sulfate, mixing the composition with an aqueous solution to obtain a paste, applying the paste to an area of bone in need of treatment, and allowing the paste to set.

The compositions that are mixed with an aqueous solution according to the invention comprise hemihydrate calcium sulfate particles having a diameter size distribution such that at least 50% of the hemihydrate calcium sulfate particles in the composition have diameters of from approximately 50 nanometers (nm) to 500 nm, inclusive (hemihydrate calcium sulfate nanoparticles).

The nanoparticles of hemihydrate calcium sulfate used in the invention can be provided in a variety of forms. For example, they can be provided as an α isoform (nCS-hemi-α), as a β isoform (nCS-hemi-β), or in combinations thereof. Generally, nCS-hemi-α crystals on average have larger diameters and are more prismatic than nCS-hemi-β, and when mixed with water, nCS-hemi-α particles form a stronger and harder superstructure. Therefore, the present invention includes compositions comprising mixtures of nCS-hemi-β and nCS-hemi-α particles in varying ratios so as to provide compositions with strengths and hardness that can be tailored for facilitating repair of varying types of bone and bone damage.

In preferred embodiments, at least 60%, 70%, 80%, 90% or 95% of the nCS hemihydrate particles in the composition have diameters of from approximately 50 nm to 500 nm.

In one embodiment, a composition that can be used for mixing with an aqueous solution comprises nCS-hemi-β particles, wherein at least 50% of the particles have diameters of from 50 nm to 250 nm.

In other embodiments, at least 60%, 70% or 80% of the nCS-hemi-β particles in the composition are characterized by diameters of from approximately 50 nm to 250 nm.

In another embodiment, the invention provides a composition comprising nCS-hemi-α particles, wherein at least 50% of the particles in the composition have diameters of from 200 nm to 500 nm.

In other embodiments, at least 50%, 60% or 70% % of the nCS-hemi-α particles in the composition have diameters of from approximately 200 nm to 400 nm.

Suitable nCS-hemi-α particles include those having a mean diameter of 336.6±72.0 nm; a range of particle diameters of 240~480 nm; and a particle diameter distribution as follows: 200~300 nm=40%; 300~400 nm=33%; 400~500 nm=27%.

Suitable nCS-hemi-β particles have a mean diameter of 110.1±64.9 nm; a range of particle diameters of 50~240 nm; and the following diameter size distribution: 50~100 nm=60%; 100~200 nm=20%; 200~250 nm=20%.

Thus, the method of the invention comprises use of calcium sulfate preparations that have significantly smaller mean diameters and distinct particle distributions as compared to conventional calcium sulfate preparations used for bone repair, wherein greater than 85% of calcium sulfate particles in the conventional preparations have diameters of over 10 microns. Conventional calcium sulfate crystals have varying sizes. The range of CS particle is normally between 1~30 μm in diameter. In connection with this, we have determined that the diameter of particles utilized in the method of the present invention is on the order of 1000 times smaller than conventional calcium sulfate preparations. This reduced scale results in an increased surface area of nCS of about 10 times greater than that of conventional, micron-sized preparations of calcium sulfate, which imparts useful properties to the compositions. For example, we demonstrate that PDGF adsorbed onto nCS-hemi-β particles is released in vitro more quickly than from a conventional calcium sulfate preparation. Therefore, it is expected that nCS-hemihydrate particles will have favorable adsorption/release characteristics for a variety of growth factors provided in combination with the particles in vivo.

We also demonstrate that use of nCS-hemi-β in a method of treating an animal model of a critical bone defect results in improved quality of healing in terms of tissue space maintenance when compared to a negative control. Moreover, in the same animal model system, we demonstrate that a composition comprising nCS-hemi-β and PDGF is more effective in treating the defect than a conventional calcium sulfate preparation.

Thus, in one embodiment, the composition applied to bone according to the method of the invention may comprise a growth factor. Suitable growth factors include but are not limited to PDGF, insulin-like growth factor (IGF-I), transforming growth factor beta (TGF-β), epidermal growth factor (EGF), and fibroblast growth factor (FGF). Growth factors suitable for use in the present invention are commercially available from a variety of vendors or may be isolated and purified from a variety of biological tissues. For instance, there are commercially available systems for delivering growth factors for bone tissue repair, such as GEM21® (β-Tri-calcium phosphate and PDGF-BB) and INFUSE® (collagen sponge and BMP-2).

In a preferred embodiment, the growth factor is PDGF. PDGF is a cationic, heat-stable protein found in the granules of circulating platelets and is known to stimulate protein synthesis and collagen production by fibroblasts. It is also known to act as a mitogen and chemotactic agent. PDGF exists as three different types dimer isomers (AA, AB, and BB).

The greater surface area of the hemi-nCS preparations provided for use in the method of the invention will provide enhanced scaffolding and improved osteoconductivity in damaged bone tissue relative to previously available techniques, and resorption and replacement of the nCS with new bone is expected to proceed at a more efficient rate. In connection with this, the invention contemplates altering various components of the composition that is applied to damaged bone to optimize not only hardness and moldability, but also the rate of growth factor release, calcium sulfate resorption and/or osteoconductivity. For example, the amount of water, growth factor, and alpha and/or beta forms of hemi-nCS can be varied to impart a wide variety off desired properties to the compositions.

Clinical uses for the present invention are expected to include but are not limited to treating any damaged area of bone. Damaged areas of bone suitable for treating with the method of the present invention could arise in: any clinical procedure where autogenous bone graft normally would be used, but an insufficient amount is available and alternative or supplemental material is needed; for repair of tumor cavities after removal of tumor; for plastic reconstructive surgery to assist new bone formation at sites where necessary; for spinal intervertebral joint fusions (disk arthroplasty) or any other joint fusions; for the replacement of necrotic bone segments; for surgical reattachment of avulsed bone fragments; for dental and orthodontic applications and maxillofacial reconstruction; and for repair of any bone fracture or other disruption of the integrity of bone tissue, all for human and/or veterinary procedures, including for all non-human vertebrates. In addition, nCS can be used for periodontal tissue regeneration around teeth; for bone defects around dental implants; for bone augmentation of alveolar ridge; alveolar socket preservation; and as in dental and medical implantation procedures.

For methods involving guided tissue regeneration (GTR), it is preferable to provide a barrier membrane to allow appropriate cell migration and proliferation in damaged areas and to prevent cell migration and tissue ingrowths to the damages area. nCS formulations provided for use in the present invention are expected to form suitable such barriers after setting of the nCS paste.

nCS hemihydrate nanoparticles for use in the invention may be provided by any suitable method. In general, the hemihydrate nCS nanoparticles can be obtained by treating conventionally sized calcium sulfate dihydrate with various methods. Conventional dihydrate calcium sulfate preparations are commercially available. They are characterized by containing a majority of calcium sulfate particles with diameters in a range of from 1-30 microns. It is preferable to use medical grade calcium sulfate as a starting material to obtain the nCS hemihydrates for use with the present invention. Medical grade dihydrate calcium sulfate can be generally characterized as having a mean particle diameter of about 4.4 microns.

Conventional dihydrate calcium sulfate can be processed to obtain nanoscale calcium sulfate dihydrate particles by either cryo-vacuum (freeze-drying) or microemulsion techniques. It is preferable to use a cryo-vacuum technique. The nanoscale calcium sulfate dihydrate particles may then be treated by autoclaving to obtain nCS-hemi-α particles, or by oven drying to obtain nCS-hemi-β particles. nCS-hemi-α particles tend to be larger in diameter than nCS-hemi-β particles and, when mixed with water, form stronger and harder structures. Thus, combinations of alpha- and beta-nCS hemihydrates can be obtained by mixing the two forms together to optimize hardness and moldability for use in the present invention.

A suitable microemulsion technique for making dihydrate nCS has been described (Rees, et al., *Langmuir* 15 (1999) 1993-2002). Briefly, the technique comprises adding calcium chloride and sodium sulfate to surfactants, oil and water to form nano-sized particles of calcium sulfate. Alternatively, reverse micelles of calcium precursor (calcium chloride) and sulfate precursor (sodium sulfate) microemulsions can be made by mixing AOT (dioctyl sulfosuccinate), dodecane and water (Rees, et al., *Langmuir* 15 (1999) 1993-2002)). The microemulsions can be evaporated until about one tenth of the original microemulsion volume remains, washed with ethanol, centrifuged to obtain a nCS hemihydrate precipitate, and dried in a fume hood. However, the microemulsion technique requires removal of solvent and tends to have poor nCS dihydrate yields. Therefore, in a preferred embodiment, dihydrate nCS are synthesized using a cryo-vacuum technique. A suitable cryo-vacuum technique has been previously described (Salvadori, et al. *Journal of Colloid and Interface Science*, 2005, 1-4) and avoids introduction of surfactants or other components beyond calcium sulfate and water. Briefly, this technique comprises quick freezing a solution of conventional CS and dehydrating the frozen ice of the solution of CS under vacuum (lyophilization). As an illustrative protocol, a master solution of CS using 8 grams of medical grade calcium sulfate dihydrate (CaSO4.2H2O) per 4 liters of distilled filtered water is prepared by stirring for at least 24 hours at room temperature. The solution is sprayed or coated on a lyophilization flask immersed in liquid nitrogen (−196° C.) for 2 minutes, which results in a sprayed or 'shell' coating of a frozen calcium sulfate solution on the interior of the lyophilization flask. The flask is placed in a lyophilization chamber under cryogenic conditions and vacuum until the frozen calcium sulfate is completely dried for various time depending on the volume of water in the flask, leaving behind a nanocrystalline powder of nCS dihydrate.

In order to form a hemihydrate, the freeze-dried crystals can be placed in a conventional heat oven and dried at 250~300° F., or at 135°~150° C. for 15 minutes or more. Oven drying produces predominantly produce nCS-hemi-β particles. The nCS-hemi-α particles can be produced by autoclaving the nCS dihydrate for about two hours or more. Either form or a combination of the forms can be mixed with an aqueous solution to produce a paste, having desired setting and moldability properties for use in the method of the present invention.

It is preferred that the hemi-nCS particles be sterilized using a glow discharge treatment (GDT). The GDT process is a well-known method for sterilizing and surface-activating a variety of ceramic, metal and plastic substrata (Baier et al., (1970) *Cornell Aeronautical Laboratory Report* no 176; Baier, (1990) *Transactions of The Academy of Dental Materials* 3:6-29). Briefly, GDT comprises placing hemi-nCS into a vacuum chamber for approximately 2 minutes and subjecting the nCS to low-temperature gas plasmas that strip away organic contaminants and improves surface-activation. GDT results in sterile nanoparticles of hemihydrate-nCS that can be mixed with an aqueous solution for use in the invention.

Compositions comprising hemi-nCS crystalline nanoparticles can be provided as pure or essentially pure calcium sulfate preparations, and may be provided in powder form, or as compressed tablets formed in any of a variety of tablet configurations, concentrations and/or weights to provide for convenient, ready-made compositions suitable for mixing with an aqueous solution for application to a damaged area of bone according to the method of the present invention.

The following Examples are intended to illustrate but not limit the invention.

Example 1

This Example provides an analyses of calcium particles present in a variety of calcium sulfate preparations. Specifically, size, shape and composition of the particles were evaluated using Scanning Electron Microscopy (SEM), Energy dispersive X-ray spectroscopy (EDS) analysis, Transmission Electron Microscopy (TEM) and Fourier Transform Infra Red spectroscopy (FTIR). Additionally, X-ray diffraction (XRD) was used to verify the components of the composition, while the Brunauer, Emmet and Teller (BET) method was employed to determine the surface area of the material.

Figure 1B:
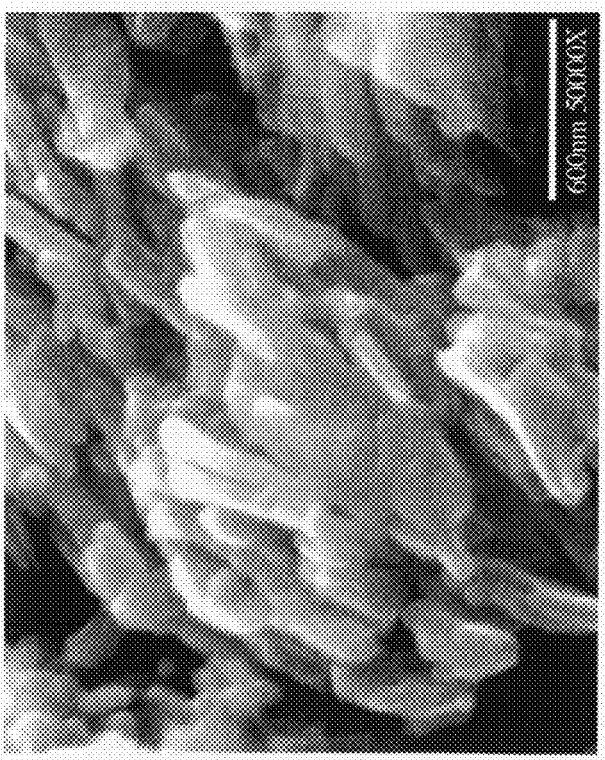

SEM analysis of commercially available alpha (α) form of calcium sulfate (CAPSET), medical grade calcium sulfate (CS), and of nCS-dihydrate, nCS-hemi in β form (nCS-hemi-β), and nCS-hemi in α form (nCS-hemi-α) was used to determine particle sizes. A representative SEM image for nCS-hemi is provided in FIGS. 1A and 1B at different magnifications. nCS-hemi-β Comparative data were obtained by determining mean crystalline particle diameters from multiple scanning electron (SEM) images for each particle type. The results are summarized in Table 1 and graphically in FIG. 2. The symbol "~" is used herein interchangeably with "about" and "approximately" when used to refer to particle size. Ranges of particle sizes are inclusive of the upper and lower limits specified.

TABLE 1

| Dependent Variable: Micrometer (μm) | | | |
|---|---|---|---|
| Group | Mean (μm) | Std. Deviation | N |
| CAPSET | 18.9839 | 5.2081 | 15 |
| CS | 4.4017 | 2.1871 | 15 |
| nCS-dihydrate | 0.0714 | 0.0344 | 15 |
| nCS-hemi-β | 0.1101 | 0.0649 | 15 |
| nCS-hemi-α | 0.3366 | 0.0720 | 15 |

ANOVA analysis and post-hoc tests using Bonferroni analysis of the data presented in Table 1 reveal that there are statistically significant differences between conventional macro-sized calcium sulfate groups (CAPSET and CS), and as between the conventional macro-sized calcium sulfate particles and the nano-sized calcium sulfate particles (nCS, nCS-hemi-β, nCS-hemi-α).

From analysis of the data presented in Table 1 and the graphical summary provided in FIG. 2, it can be determined that CAPSET particles have a mean diameter of 18.98±5.2 µm; a range of particle diameters of 9~28 µm; and the following diameter size distribution: less than 10 µm=13%; 10~20 µm=27%; 20~30 µm=60%.

CS particles have a mean diameter of 4.4±2.2 µm; a range of particle diameters of 2~10 µm; and the following diameter size distribution: 2~5 µm=73%; 5~10 µm=27%.

nCS-dihydrate particles have a mean diameter of 71.4±34.4 nm; a range of particle diameters of 24~130 nm; and the following diameter size distribution: 20~50 nm=27%; 50~100 nm=46%; 100~130 nm=27%. We have determined that the nCS-dihydrate particles, when mixed with an aqueous solution, are less moldable than the hemihydrate particles.

nCS-hemi-β particles have a mean diameter of 110.1±64.9 nm; a range of particle diameters of 50~240 nm; and the following diameter size distribution: 50~100 nm=60%; 100~200 nm=20%; 200~250 nm=20%.

nCS-hemi-α particles have a mean diameter of 336.6±72.0 nm; a range of particle diameters of 240~480 nm; and the following particle diameter distribution: 200~300 nm=40%; 300~400 nm=33%; 400~500 nm=27%.

Thus, it will be recognized from the foregoing data that compositions comprising nCS-hemi particles can be provided with a wide variety of diameter size distributions, including but not limited to compositions comprising nCS-hemi particles, wherein at least 50%, 60%, 70%, 80%, 90% or 95% of the nCS-hemi particles in the compositions have diameters of from approximately 50 nm to 500 nm. Such compositions may comprise nCS-hemi-β, nCS-hemi-α and combinations thereof and are used for mixing with water to form the paste that is applied according to the method of the invention.

Figure 3:
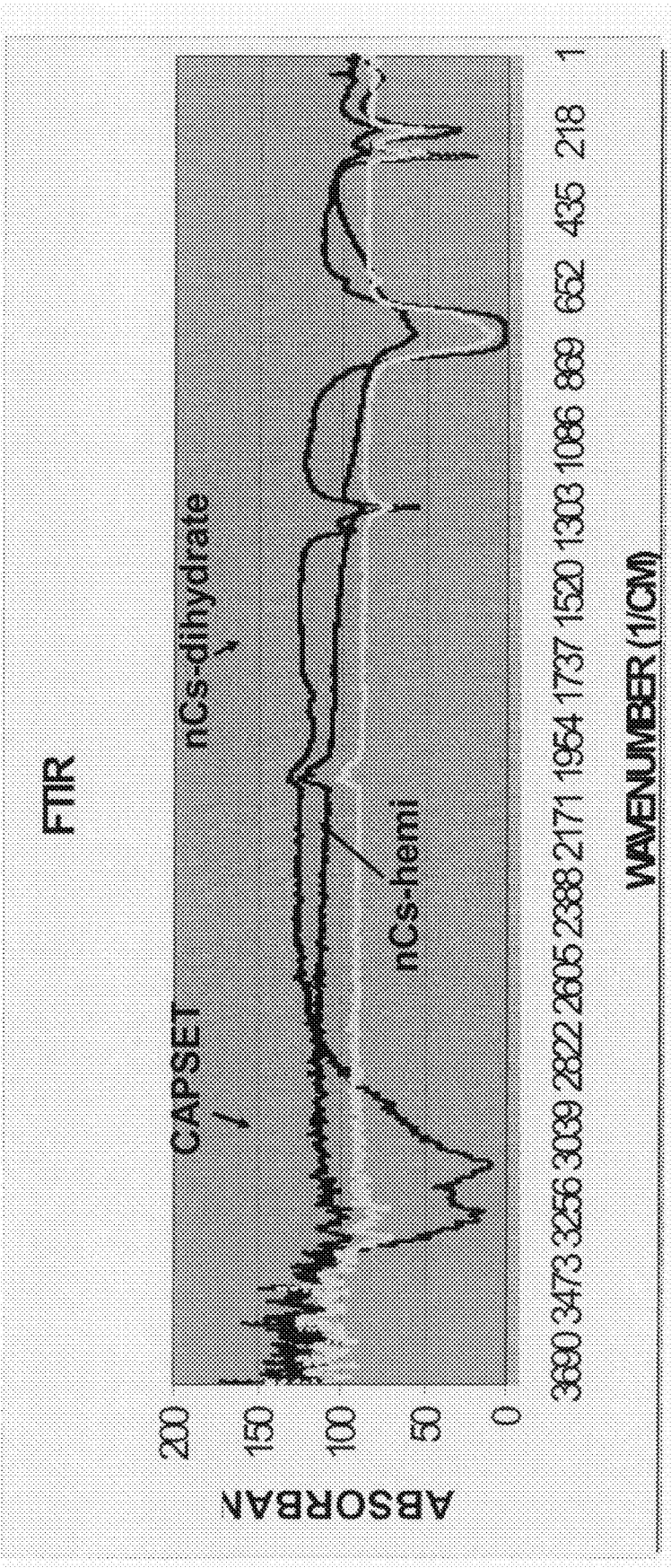
FIG. 3 provides a graphical representation of an FTIR analysis of CAPSET, nCS-dihydrate and nCS-hemi-β.

FIG. 3 provides an FTIR analysis of CAPSET, nCS-dihydrate and nCS-hemi-β. The results confirm that nCS-dihydrate is associated with 2 water molecules and CAPSET (CS-hemi-α) and nCS-hemi-β lose water molecules and have are associated with ½ water molecule.

Figure 4A:
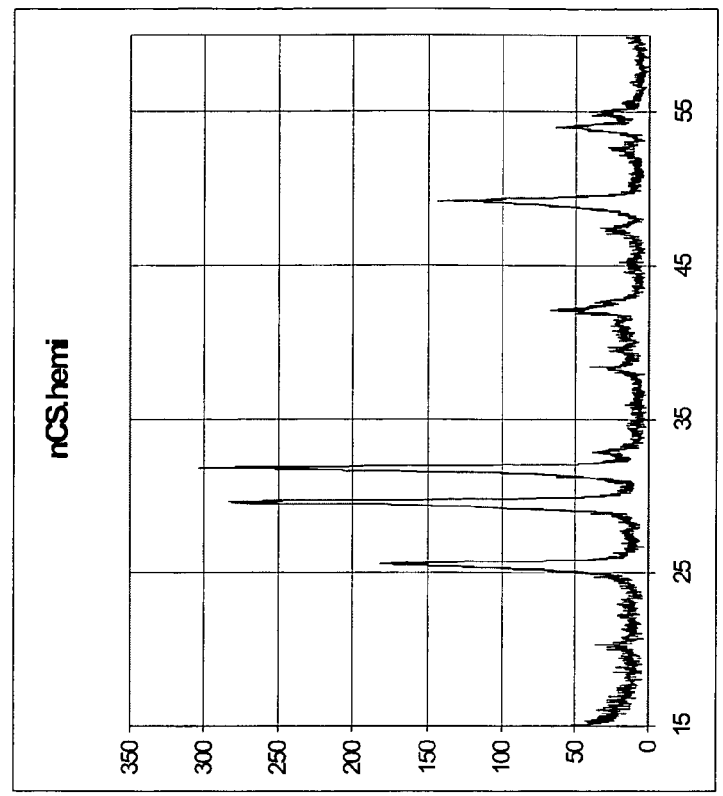
FIGS. 4A and 4B provides graphical representations of X-Ray Diffraction (XRD) analysis which confirm that nCS-hemi-β (FIG. 4B) provided for use in the present invention is distinct from the dihydrate form (FIG. 4A).
Figure 4B:
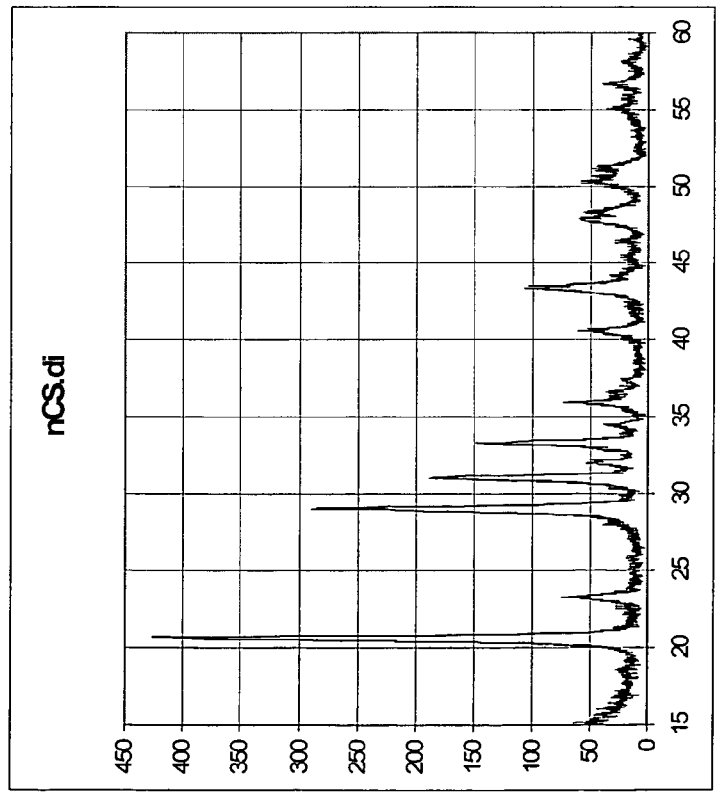

FIGS. 4A and 4B provides XRD confirmation that nCS-hemi-β (FIG. 4B) provided for use in the present invention is distinct from the dihydrate form (FIG. 4A).

Figure 5:
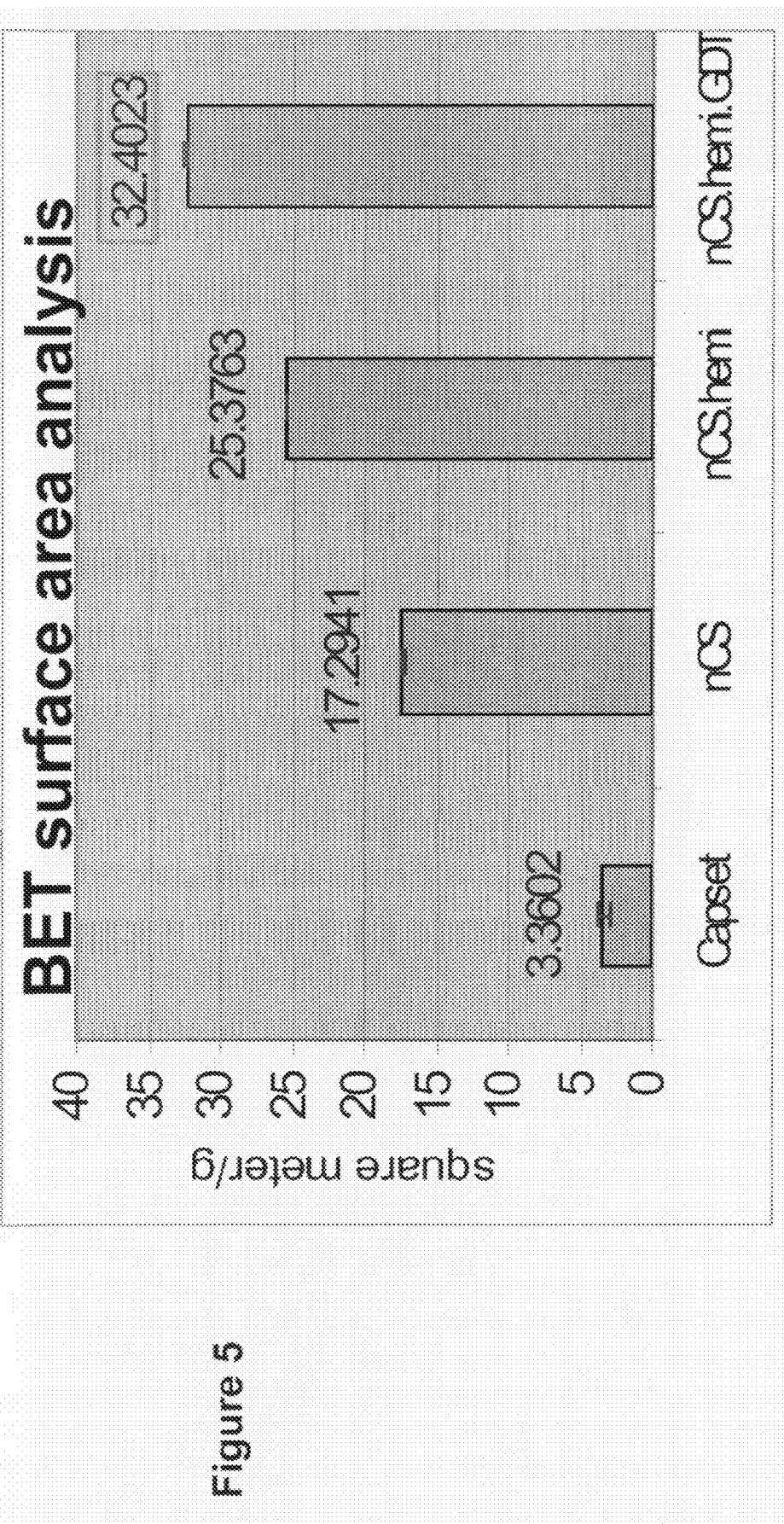
FIG. 5 provides a graphical summary of Brunauer, Emmett, and Teller (BET) surface area analysis of CAPSAT compared to nCS-dihydrate, nCS-hemi-β, and nCS-hemi-β, treated by glow discharge treatment (GDT).

FIG. 5 provides a graphical summary of Brunauer, Emmett, and Teller (BET) surface area analysis of CAPSAT compared to nCS-dihydrate, nCS-hemi-β and nCS-hemi-β treated by glow discharge treatment (GDT). These data demonstrate that nanoparticulate calcium sulfate suitable for use in the method of the present invention has a 5 to 10 fold greater surface area than CAPSET. The greater surface area is believed to allow for greater scaffolding ability of the material due to higher surface area for attachment of osseous cells and for more efficient osteoconductivity as cells gather at sites where regeneration is initiated.

Figure 6:
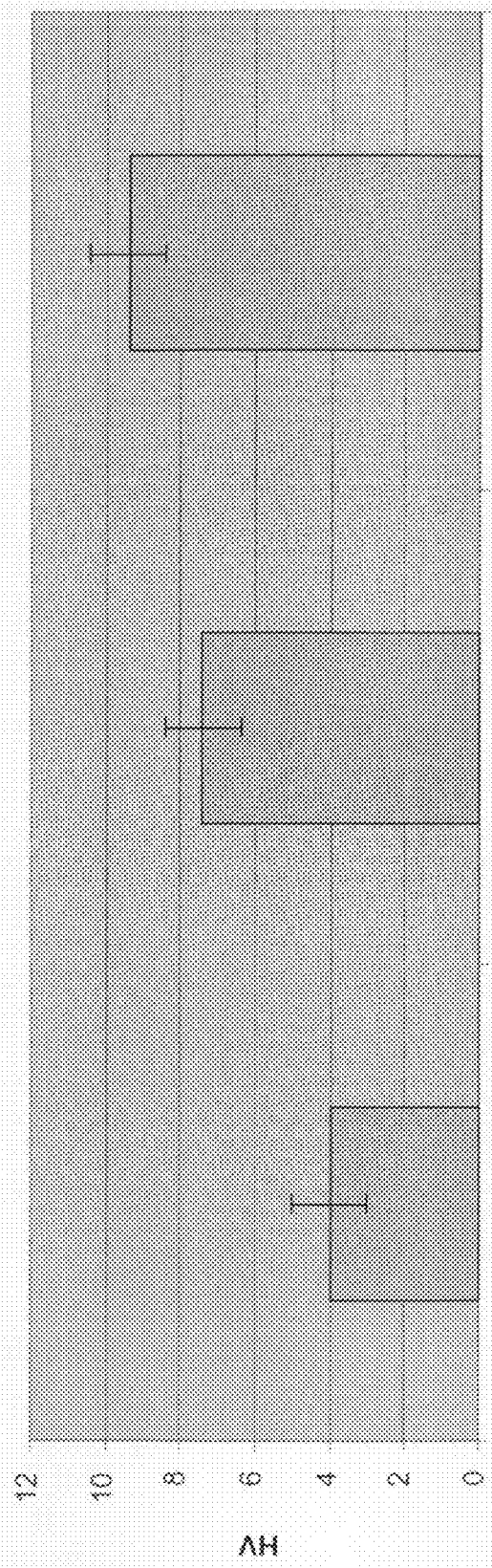
FIG. 6 provides a graphical representation Vickers hardness analysis for conventional CS, nCS-hemi, and a combination of 70% nCS-hemi-β and 30% of nCS-hemi-α by weight.

FIG. 6 provides a measurement of microhardness conventionally referred to as "Vickers hardness." The Vickers test has one of the widest scales among hardness tests. The hardness number is determined by the load over the projected area of the indentation. The results show that the combination of nCS-hemi-α and β has the highest hardness. The nCS-hemi-β is second ranked and conventional CS has the lowest hardness, which is 2 fold less than the nCS-hemi-α and β combination. Both the combination and nCS-hemi-α and β show higher hardness than CS.

Example 2

This Example provides a description of data supporting biocompatibility and safety of nCS-hemi-β for use in the present invention.

Primary human osteoblasts, gingival fibroblasts, and MMC53 cells which are derived from multiple myeloma patient bone marrow were seeded onto 12 well plates with α-MEM supplemented with FCS (10%), L-glutamine (2 µmol/ml), penicillin G (100 U/ml), streptomycin sulfate (100 µg/ml) and amphotericin B (0.25 µg/ml), and incubated for 2 days. In the presence of nCS, osteoblasts, gingival fibroblasts, and MMC53 showed no cytotoxicity at low dose of nCS as measured by the MTT (3-(4,5-dimathyl-thiazol-2-yl)-2,5-diphenyl tetrazolium bromide) assay and ALP (Alkaline Phosphatase Activity). Further, there were no inhibitory cell responses, and the results were similar among the different cell types tested.

We also analyzed whether osteoblasts express Collagen type I (Col), Bone Sialoprotein (BSP), and Alkaline phosphatase (ALP) in the presence of nCS. Specifically, primary human osteoblasts were grown in α-MEM supplemented with FCS (10%), L-glutamine (2 µmol/ml), penicillin G (100 U/ml), streptomycin sulfate (100 µg/ml) and amphotericin B (0.25 µg/ml), and treated with 0 (control), 0.01, 0.1, 1.0, 100 and 1000 µg/ml of nCS-hemi-β for 24 hours. RT-PCR analysis revealed the expression of alkaline phosphatase (ALP), Type I collagen (COL) and bone sialoprotein (BSP) in the presence of various concentrations of nCS. Low concentrations of nCS appeared to induce the expression of Type I collagen and bone sialoprotein whilst higher concentrations of nCS appeared to strongly induce alkaline phosphatase and to inhibit bone sialoprotein. RT-PCR analysis shows that there are dose dependent effects of nCS-hemi-β on differentiation of osteoblasts.

Example 3

This Example provides a demonstration that nCS-hemi particles used in the present method have superior growth factor release properties than conventional calcium sulfate preparations.

To obtain the data presented in this Example, 100 mg samples of nano-calcium and conventional calcium sulfate (nCS-hemi-β; CAPSET) were mixed with 50 µl solution of radioactive PDGF-BB, and then placed in separate microfuge tubes. The supernatants were removed and the pellets washed twice with 0.5 ml of cold PBS. The samples were transferred to fresh sterile microfuge tubes and incubated in 100 µl PBS at room temperature for 20 days. The time 0 points were executed as quickly as manually possible in order to measure the amount of radioactivity of PDGF originally inserted. After each daily time point, the supernatant was removed from the appropriate sample and washed twice. The amount of retained radiolabeled PDGF was measured using a gamma spectrometer. The amount of growth factor released from the matrix material was calculated as a percent of the amount which had originally inserted.

Figure 7:
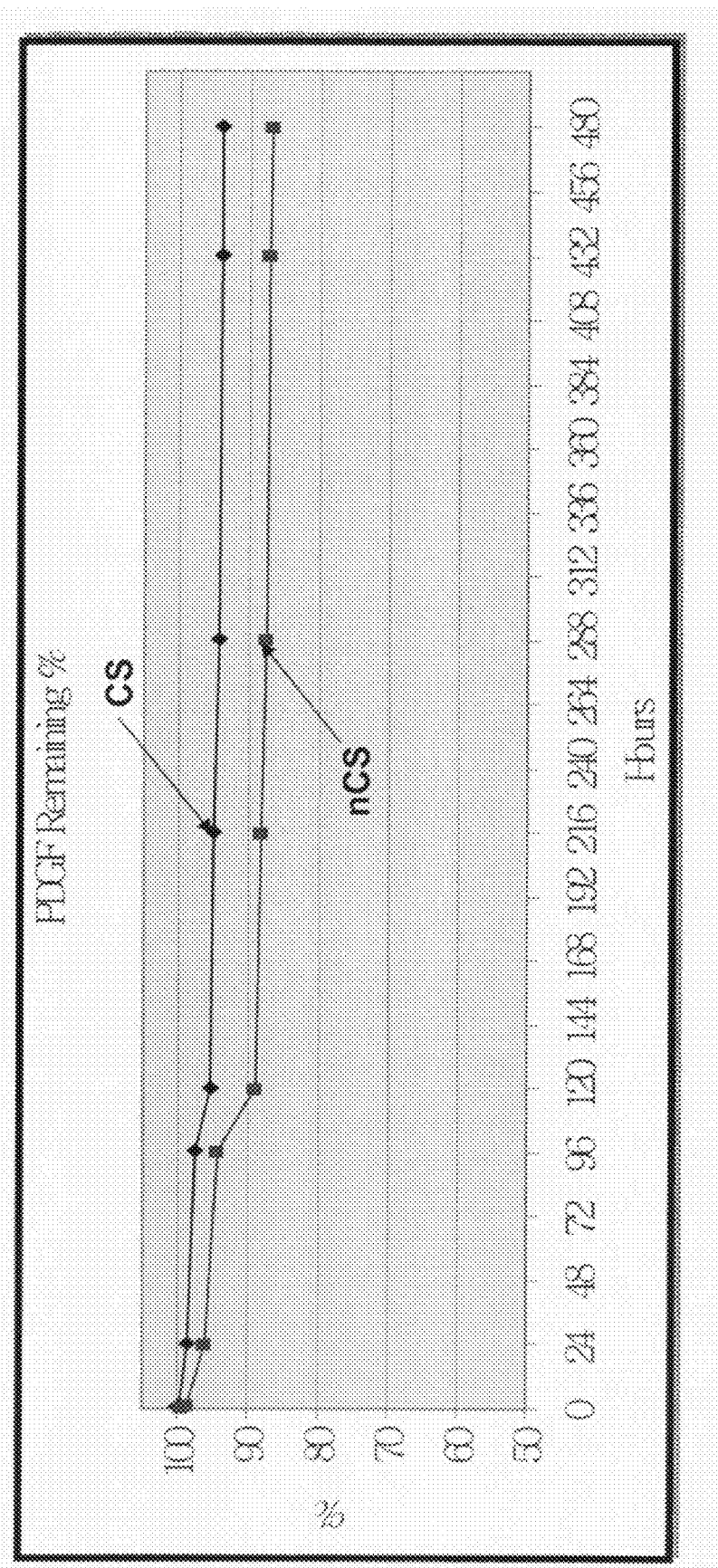
FIG. 7 provides a graphical representation of data which demonstrates that nCS-hemi-β releases more PDGF than conventional CS over time in vitro.

The results presented in FIG. 7 demonstrate that the release of PDGF is directly proportional to dissociation of the materials. There was a degradation (dissociation) rate difference between nCS and CAPSET. nCS pallets were degraded faster than CAPSET. It is presumed this is because the surface area of nCS is larger than CAPSET, which results in more interaction with the PBS solution. The degraded nCS particles accordingly released more PDGF, which was entrapped among particles or absorbed on the particle surfaces of nCS) Thus, nCS is demonstrated releases more PDGF that conventional CS.

Example 4

This Example demonstrates using the method of the invention in the calvarial rat defect model, which is a well studied model that allows in vivo testing of the ability of a material to treat a critical size defect and to analyze histologically the in situ cellular response to the materials placed in the site (Perinpanayagam, et al. Archives of Oral Biology, 2006, 51, 406; Rauschmann, et al., Biomaterials, 2005, 2677-2684). The model permits materials to be tested for a potential/inflammatory response as well to quantify the osseous conductive/inductive effect.

For this Example, we used male Sprague-Dawley rats weighing 300-350 gm. All housing and management, experimental and surgical procedures were approved by the Institutional Animal Care Committee of the University at Buffalo. Immediately before surgery, each animal was given a subcutaneous injection of buprenoprhine (0.15 mg/kg). Animals were induced with 5% isoflurane/$O_2$ gas mixture administrated by a non-rebreather anesthesia circuit. After induction, the incision site and surrounding area was shaved and cleaned with povidine iodine solution. For the remainder of the surgery, the animals were maintained on a 2% isoflurane/$O_2$ gas mixture. A midline incision in the skin over the cranium was made in each rat from the middle of the nasal bones to the posterior nuchal line. The periosteum underneath was incised and dissected. An 8 mm craniotomy was made with a low speed handpiece and a trephine burr (drill). The drilling site was irrigated with saline. A weighed amount of a composition comprising nCS-hemi-β (100 mg) mixed with aqueous solution (distilled water 60 µl) with or without growth factor (PDGF-BB) was applied to the damaged area in each experimental animal. In the negative control group, the damaged area was left untreated. The overlying tissues were closed in layers with resorbable 5-0 Vicryl® sutures. After surgery, the animals were housed individually in plastic cages and provided with a soft diet and water.

Each treatment was evaluated after 8 and 12 weeks where at each time point the rats were euthanized by $CO_2$ asphyxiation. The craniotomy sites with 10 mm contiguous bone were recovered from the skull and placed in 10% buffered neutral formalin. The calvaria were taken x-ray using dental x-ray system at 70 kV, 10 mA and 3/60 second. The x-ray film images were scanned and analyzed. New bone formation and/or calcium sulfate scaffolding was analyzed by measuring the region of new bone in the critical size defect using A4i image analysis software. The volume, surface, and density of the newly regenerated bone were measured. After x-ray images quantification, the specimens were processed for demineralized tissue sectioning (4 micron) and H & E (hematoxylin and eosion) staining.

Figure 8:
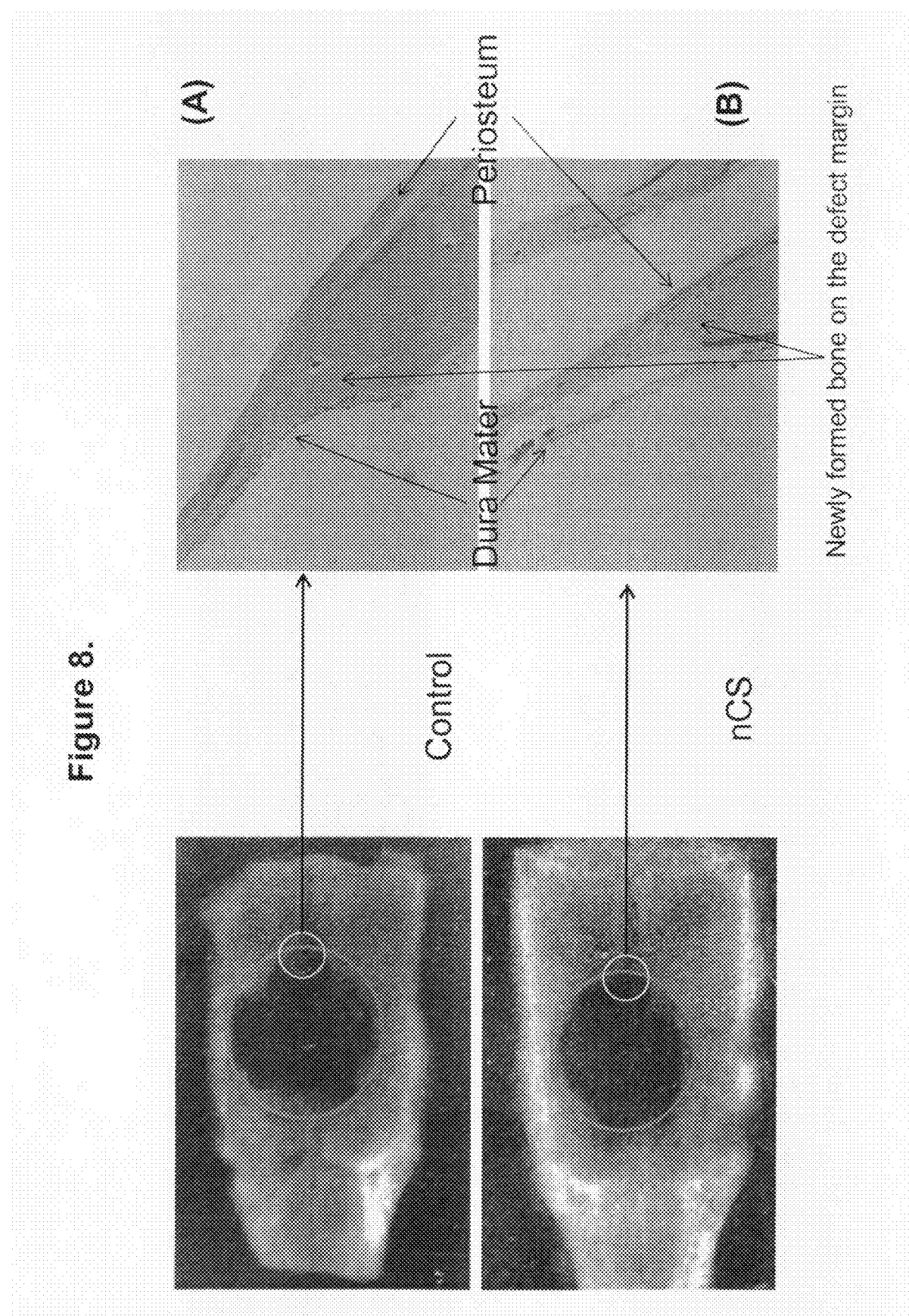
FIG. 8 provides photographic representations of X-ray images and histological analysis of a bone defect in an animal model treated in accordance with the method of the invention.
Figure 9:
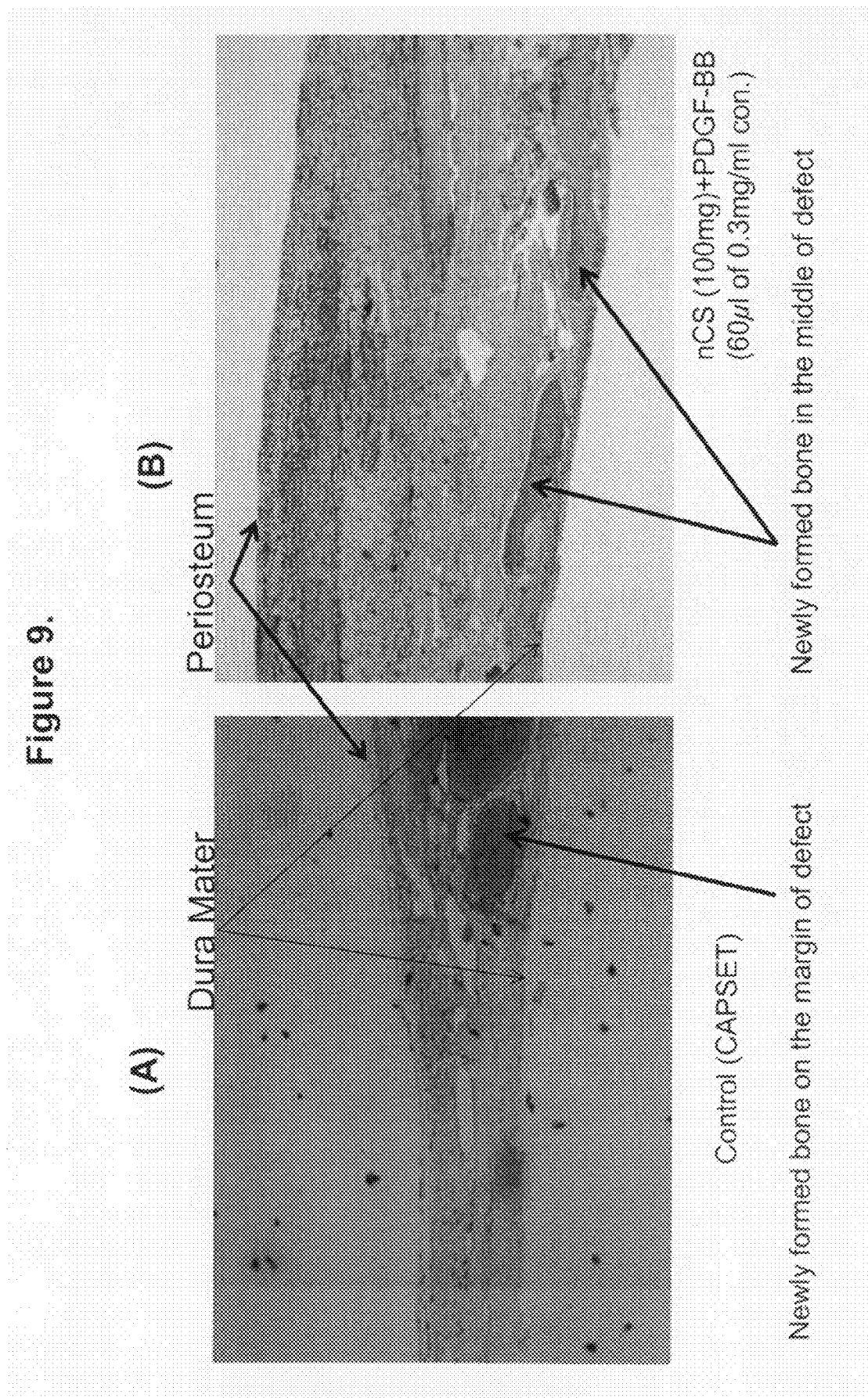
FIG. 9 provides a photographic representation of histological analysis of a bone defect treated in an animal model with CAPSET alone (panel A) and nCS-hemi-β+PDGF in its BB isoform (panel B).

The results are presented in FIGS. 8 and 9 and demonstrate that after 12 weeks, there is no detectable difference in bone formation between the control group and experimental group (FIG. 8, panel A and B). However, treatment with nCS-hemi-β results in improved quality of healing in respect of tissue space maintenance when compared to the negative control (i.e., no calcium sulfate treatment); (FIG. 8, panel B). Further, treatment with CAPSET alone (FIG. 9, panel A) shows no detectable bone growth, while FIG. 9, panel B, illustrates substantial growth in the defect for when nCS-hemi-β+PDGF-BB is used. Thus, compositions comprising nCS-hemi-β and optionally growth factors are demonstrated to be effective for treating bone defects in vivo.

We claim:

1. A method for facilitating repair of a damaged area of bone comprising:
   i) providing a composition comprising hemihydrate calcium sulfate particles, wherein at least 50% of the particles of hemihydrate calcium sulfate in the composition have a diameter of from 50 nanometers (nm) to 500 nm;
   ii) mixing the composition with an aqueous solution to obtain a paste;
   iii) applying the paste to the damaged area of bone; and
   iv) allowing the paste to set to facilitate repair of the damaged area of bone.

2. The method of claim 1, wherein at least 60%, 70%, 80%, 90% or 95% of the particles of hemihydrate calcium sulfate in the composition have a diameter of from 50 nm to 500 nm.

3. The method of claim 1, wherein the particles of hemihydrate calcium are provided in an α isoform (nCS-hemi-α particles), as a β isoform (nCS-hemi-β particles), or as a combination thereof.

4. The method of claim 3, wherein the composition comprises nCS-hemi-β particles, and wherein at least 50% of the nCS-hemi-β particles in the composition have diameters of from 50 nm to 250 nm.

5. The method of claim 4, wherein at least 60%, 70% or 80% of the nCS-hemi-β particles in the composition have diameters of from 50 nm to 250 nm.

6. The method of claim 3, wherein the composition comprises nCS-hemi-α particles, and wherein at least 50% of the nCS-hemi-α particles in the composition have diameters of from 200 nm to 500 nm.

7. The method of claim 6, wherein at least 60% or 70% of the nCS-hemi-α particles in the composition have diameters of from 200 nm to 400 nm.

8. The method of claim 1, wherein the composition further comprises a growth factor.

9. The method of claim 8, wherein the growth factor is selected from the group of growth factors consisting of platelet-derived growth factor (PDGF), insulin-like growth factor (IGF-I), transforming growth factor beta (TGF-β), epidermal growth factor (EGF), and fibroblast growth factor (FGF).

10. The method of claim 8, wherein the growth factor is PDGF.

11. The method of claim 1, wherein the damaged area of bone is present in a human individual.

12. The method of claim 1, wherein the damaged area of bone is present in a non-human vertebrate.

13. The method of claim 1, wherein the composition comprising hemihydrate calcium sulfate particles is provided as a compressed tablet.

14. The method of claim 1, wherein the aqueous solution is water.

15. The method of claim 1, wherein the paste is applied to a damaged area of bone in combination with an autogenous bone graft, or in a tumor cavity created by resection of a tumor, or to a damaged area of bone during a plastic reconstruction of a damaged area of bone, or to a damaged area of bone in a joint during a joint fusion procedure, or to a damaged area of bone during surgical reattachment of an avulsed bone fragment to a damage area of bone, or to a damaged area of bone during a dental and/or orthodontic procedure, or combinations thereof.

* * * * *